(12) United States Patent
Johnson et al.

(10) Patent No.: US 6,673,239 B2
(45) Date of Patent: Jan. 6, 2004

(54) HYDROCARBON PURIFICATIN SYSTEM REGENERATION

(75) Inventors: Marvin M. Johnson, Bartlesville, OK (US); Bruce B. Randolph, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 147 days.

(21) Appl. No.: 09/747,710

(22) Filed: Dec. 21, 2000

(65) Prior Publication Data
US 2002/0112992 A1 Aug. 22, 2002

(51) Int. Cl.[7] .......................... C10G 25/12; C10G 25/02
(52) U.S. Cl. ..................... 208/305; 208/306; 208/248; 208/250; 208/254 R; 208/299; 208/187; 208/188; 502/31
(58) Field of Search ................ 208/305, 248, 208/250, 299, 254 R, 187, 188, 306; 502/31

(56) References Cited

U.S. PATENT DOCUMENTS

| | | | | |
|---|---|---|---|---|
| 3,894,090 A | | 7/1975 | Cleveland | 260/671 R |
| 5,271,835 A | * | 12/1993 | Gorawara et al. | 208/228 |
| 5,374,596 A | | 12/1994 | Marquez et al. | 502/29 |
| 5,582,819 A | * | 12/1996 | Shul et al. | 423/705 |
| 5,730,860 A | | 3/1998 | Irvine | 208/213 |
| 6,110,258 A | * | 8/2000 | Fraenkel et al. | 95/117 |

* cited by examiner

*Primary Examiner*—Walter D. Griffin
(74) *Attorney, Agent, or Firm*—Jeffrey R. Anderson; Bronwyn A. Welvaert

(57) ABSTRACT

A system and process for removing water and heteroatom-containing compounds from hydrocarbons and for regenerating the adsorbent used in the system and process is disclosed and includes contacting the hydrocarbon stream with a water adsorbent and a heteroatom-containing compound adsorbent. The regeneration includes passing an isoparaffin over the water-adsorbent, then passing the isoparaffin over the heteroatom-containing compound adsorbent; and, optionally; cooling the effluent; separating such into a hydrocarbon phase and a water phase in a settler; removing a portion of the hydrocarbon phase for mixing with water; returning the hydrocarbon/water mixture to the settler; removing some of the hydrocarbon phase from the settler to form a recycle isoparaffin stream for use as a portion of the stripping stream; and removal of a portion of the water phase from the settler to form a waste water stream containing water and heteroatom-containing compound.

62 Claims, 1 Drawing Sheet

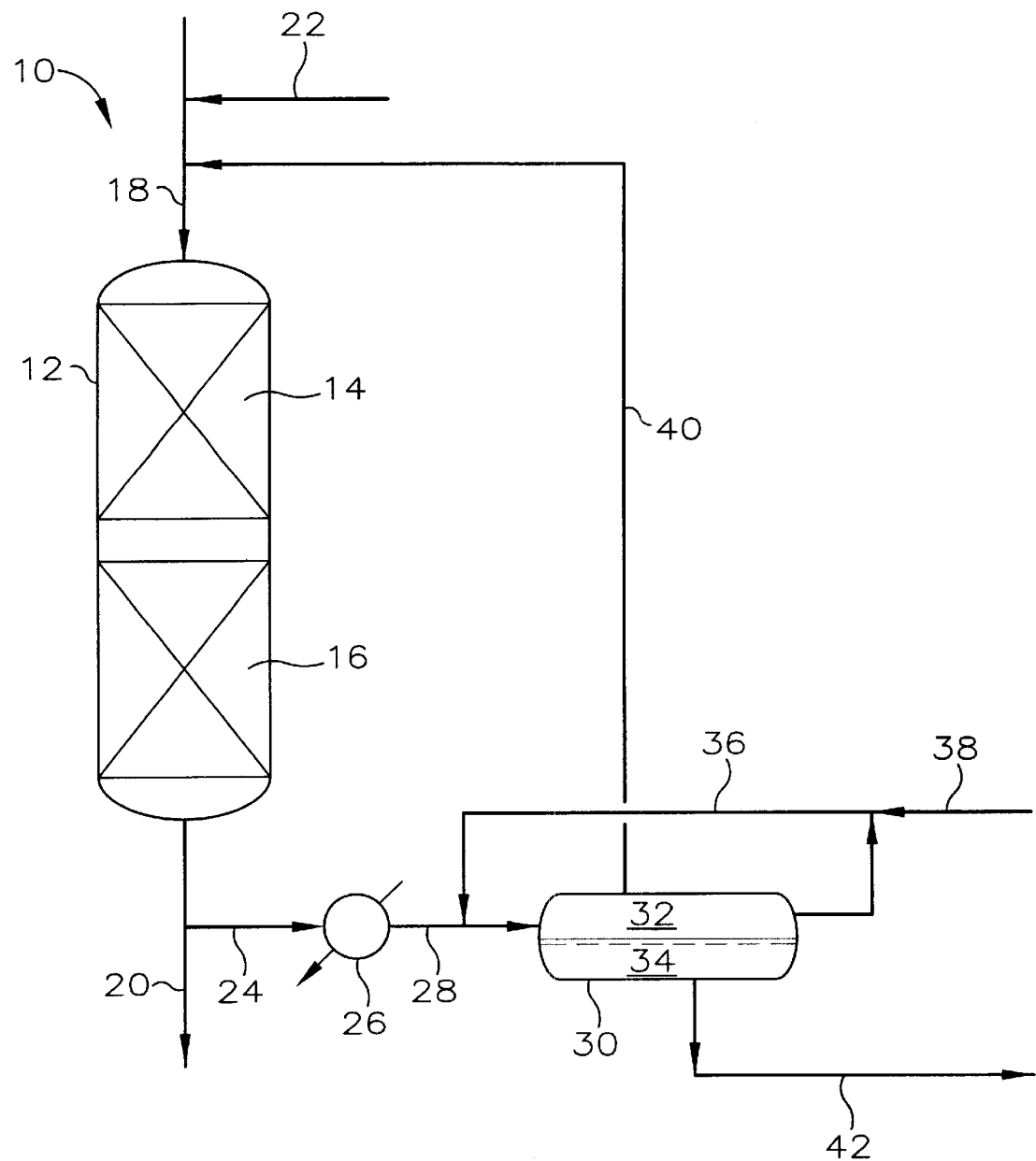

HYDROCARBON PURIFICATIN SYSTEM REGENERATION

The present invention relates to the field of hydrocarbon purification. In another aspect, the invention relates to a method for regenerating a purification system suitable for removing water and heteroatom-containing compounds from hydrocarbons.

BACKGROUND OF THE INVENTION

The presence of water and/or heteroatom-containing compounds can pose a problem in various hydrocarbon conversion processes. Included among these processes is the alkylation of olefins with saturated hydrocarbons, such as isoparaffins, by contacting the reactants with an acid catalyst to form a reaction mixture, settling the reaction mixture to separate the catalyst from the hydrocarbons and further separating the alkylation reactor effluent to recover the separate product streams. In typical alkylation units, the unreacted isoparaffin and olefin feeds are recycled to the alkylation reactor for recontact with the acid catalyst. An undesirable result of such recycle is the buildup of water and/or heteroatom-containing compounds in the isoparaffin and olefin streams.

The presence of water and/or heteroatom-containing compounds in the olefin or isoparaffin streams can cause lower alkylate octane and phase separation problems in the acid recovery section of the alkylation unit.

Therefore, development of a more efficient process for regenerating a hydrocarbon purification system suitable for removing water and heteroatom-containing compounds from hydrocarbons would be a significant contribution to the art and to the economy.

BRIEF SUMMARY OF THE INVENTION

It is, thus, an object of the present invention to provide an improved method/system for regenerating a hydrocarbon purification system suitable for removing water and/or a heteroatom-containing compound from a hydrocarbon stream, which is economical in construction and efficient in operation.

A further object of the present invention is to provide a method of treating a hydrocarbon stream containing at least one heteroatom-containing compound and water using a purification system, wherein the method includes an improved method for regenerating the purification system by removing accumulated water and heteroatom-containing compound.

In accordance with the present invention, a method of regenerating a hydrocarbon purification system is provided and includes the steps of:

(a) introducing a stripping stream comprising an isoparaffin into the contacting zone of a treatment system containing (1) a water adsorbent containing water, and (2) a heteroatom-containing compound adsorbent containing a heteroatom-containing compound; such that the stripping stream contacts the water adsorbent prior to contacting the heteroatom-containing compound adsorbent;

(b) withdrawing a spent stripping stream comprising isoparaffin, heteroatom-containing compound and water from the contacting zone; and, optionally, further including the steps of:

(c) cooling the spent stripping stream to form a cooled spent stripping stream;

(d) introducing the cooled spent stripping stream to a settler for separation into a hydrocarbon phase and a water phase;

(e) removing a portion of the hydrocarbon phase from the settler to form a circulating hydrocarbon stream;

(f) mixing the circulating hydrocarbon stream with water to form a hydrocarbon/water mixture;

(g) introducing the hydrocarbon/water mixture to the settler for separation into the hydrocarbon phase and the water phase;

(h) removing a portion of the hydrocarbon phase from the settler to form a recycle isoparaffin stream, wherein the recycle isoparaffin stream contains less water and less heteroatom-containing compound as compared to the cooled spent stripping stream; and (i) using at least a portion of the recycle isoparaffin stream as at least a portion of the stripping stream.

Other objects and advantages of the invention will be apparent from the detailed description of the invention and the appended claims.

BRIEF DESCRIPTION OF THE DRAWING

The FIGURE is a schematic flow diagram presenting an embodiment of the present invention.

DETAILED DESCRIPTION OF THE INVENTION

The hydrocarbon purification system suitable for use in the present invention contains an adsorption system within a contacting zone which can comprise, consist of, or consist essentially of a water adsorbent and a heteroatom-containing compound adsorbent.

Any material suitable for use in removing water from a hydrocarbon stream can be used as the water adsorbent in the present invention. Suitable water adsorbents include, but are not limited to, aluminas, silicates, aluminosilicates, carbons, and mixtures of any two or more thereof. Preferred water adsorbents include molecular sieves, silica gel, chabazite and clay. The most preferred water adsorbents are molecular sieves which have an average pore diameter in the range of from about 3 to about 4 Å.

Any material suitable for use in removing a heteroatom-containing compound from a hydrocarbon stream can be used as the hereroatom-containing compound adsorbent in the present invention. Suitable heteroatom-containing compound adsorbents include aluminas, zeolites, and combinations thereof. The most preferred heteroatom-containing compound adsorbent is a composition comprising an alumina and a zeolite.

The hydrocarbon stream suitable for treatment (purification) in the purification system can be any hydrocarbon stream requiring treatment to remove water and/or a heteroatom-containing compound. Typical hydrocarbon streams include, but are not limited to, alkylation unit feeds such as an olefin and/or an isoparaffin.

Referring to the FIGURE, therein is illustrated the inventive purification process/system 10 wherein the hydrocarbon stream, as described above, is introduced to the purification system 12, for contact with the water adsorbent 14 and the heteroatom-containing compound adsorbent 16, via conduit 18 which is connected in fluid flow communication with purification system 12. An effluent stream can be withdrawn from purification system 12 via conduit 20, which is connected in fluid flow communication with purification system 12, wherein the effluent stream generally contains less heteroatom-containing compound and less water than the hydrocarbon stream. The purification system can be operated in this manner until the adsorbents are saturated with water and/or heteroatom-containing compound or until the levels of water and/or heteroatom-containing compound in the effluent stream exceed acceptable levels.

At such time, the introduction of the hydrocarbon stream to the purification system 12 via conduit 18 is blocked.

Regeneration of the purification system 12 using the inventive regeneration method is accomplished by introducing a stripping stream comprising an isoparaffin to the contacting zone of purification system 12 via conduit 18 and conduit 22, which is connected in fluid flow communication with conduit 18. The stripping stream contacts the water adsorbent 14 prior to contact with the heteroatom-containing compound adsorbent 16. The isoparaffin useful as a stripping stream in the present invention can contain in the range of from 3 to 5 carbon atoms per molecule, and can be mixtures thereof. In addition, the isoparaffin useful as a stripping stream is preferably substantially free of a heteroatom-containing compound and water.

The temperature of the stripping stream is generally in the range of from about 350° F. to about 500° F.; preferably from about 375° F. to about 450° F., and most preferably from 390° F. to 425° F. The time period for contacting the stripping stream with the water adsorbent and the heteroatom-containing compound adsorbent is generally in the range of from about 0.2 to about 4 hours; preferably from about 0.3 to about 3 hours; and most preferably from 0.5 to 2 hours. Time for stripping depends on how rapidly the bed reaches 400+° F. which varies with the inlet temperature and space velocity of the stripping stream.

A spent stripping stream comprising isoparaffin, heteroatom-containing compound and water is withdrawn from the contacting zone of purification system 12 via conduit 20 and conduit 24, which is connected in fluid flow communication with conduit 20 and with a cooler 26. The spent stripping stream is optionally sent to cooler 26 for cooling to form a cooled spent stripping stream. The cooling of the spent stripping stream is preferably such that substantial portions of the water and of the heteroatom-containing compound contained in the spent stripping stream are condensed.

The cooled spent stripping stream is withdrawn from cooler 26 via conduit 28, which is connected in fluid flow communication to cooler 26 and a settler 30. The cooled spent stripping stream is introduced to settler 30 via conduit 28 and is separated into a hydrocarbon phase 32 and a water phase 34.

The hydrocarbon phase 32 can comprise vaporous and/or liquid isoparaffin.

A portion of the hydrocarbon phase 32 can be removed from settler 30 via conduit 36, which is connected to settler 30 in fluid flow communication, to form a circulating hydrocarbon stream which can comprise isoparaffin and heteroatom-containing compound. The circulating hydrocarbon stream is then mixed with a water stream, introduced to conduit 36 via conduit 38, which is connected in fluid flow communication with conduit 36, to form a hydrocarbon/water mixture.

Conduit 36 is connected in fluid flow communication with conduit 28, and the hydrocarbon/water mixture is introduced to settler 30 via conduit 36 and conduit 28 for separation into the hydrocarbon phase 32 and into the water phase 34.

A portion of the hydrocarbon phase 32 is removed from settler 30 via conduit 40, which is connected in fluid flow communication with settler 30, to form a recycle isoparaffin stream. The recycle isoparaffin stream generally contains less water and less heteroatom-containing compound as compared to the cooled spent stripping stream. At least a portion of the recycle stream is used as at least a portion of the stripping stream and is introduced to purification system 12 via conduit 18 and conduit 40, which is connected in fluid flow communication with conduit 18.

In addition, at least a portion of water phase 34 can be removed from settler 30 via conduit 42, which is connected in fluid flow communication with settler 30, to form a waste water stream comprising water and heteroatom-containing compound.

After regeneration of the purification system is complete, such as when sufficient water and/or heteroatom-containing compound has been removed from purification system 12, the introduction of the stripping stream to the contacting zone of purification system 12 via conduits 22, 40 and 18 is blocked and the introduction of the hydrocarbon stream to the contacting zone of purification system 12, via conduit 18, is restarted. The withdrawing of the effluent stream from the contacting zone of purification system 12, via conduit 20, is also restarted, thus returning the purification system back to normal operation (that is, water and/or heteroatom-containing compound removal).

The heteroatom-containing compound can be any heteroatom-containing compound typically present in hydrocarbon streams. More particularly, the heteroatom-containing compound can contain an element selected from the group consisting of sulfur, nitrogen, oxygen, and combinations of any two or more thereof. More typically, the heteroatom-containing compound is a compound selected from the group consisting of acetonitrile, acetone, and combinations thereof.

The following example is provided to further illustrate this invention and is not to be considered as unduly limiting the scope of this invention.

EXAMPLE

A tubular reactor was charged with 6.1 g (8.5 mL) of molecular sieve 3A, (obtained from Aldrich Chemical Co. under product designation Molecular Sieves 3A) and 6.26 g (8.5 mL) of Selexsorb adsorbent, obtained from Alcoa Corp., Pittsburgh, Pa., under product designation Selexsorb CD. The two adsorbants were separated from each other with Alundum alumina (inert, low surface area alumina) and the remainder of the reactor was charged with Alundum alumina. The molecular sieve and Selexsorb adsorbent were then heated to 425° F. under N2 gas purge for 1 hour.

A feed blend was prepared containing 54.6 g propylene, 245.2 g 2-butenes, 0.40 g acetonitrile and 0.11 g water. This feed was then shaken and charged to a syringe pump. A 28.69 g portion was pumped into a cylinder and was extracted with 26.54 g distilled water. The water extract was analyzed by gas chromatography for acetontrile. By correction, the feed, as charged, contained 605 ppm acetonitrile. Results are given in the Table.

The reactor was held at 90° F. and the feed was pumped through the reactor at a rate of 130 mL/hour. System pressure was constant at 100 psig (N2). Samples of reactor effluent were captured at 2 and 4 hours time on stream (TOS). These samples were extracted with a known amount of water and the water extracts analyzed by GC for acetonitrile. Results are given in the Table.

The feed was then stopped and the system purged with N2 from the pump inlet to the liquid collector for 3 hours. The N2 was bubbled through distilled water (25.0 mL) placed in the liquid collector.

At this time, pure isopentane (iC5) was charged to the feed pump. The reactor heater control was set initially to 425° F. The iC5 was then charged to the reactor (0 psig N2) and samples of condensed iC5 in the liquid receiver were collected, extracted with water, and the water analyzed for acetonitrile. The results are given in the Table. The temperature set point had to be continually raised to maintain reactor temperature, since the iC5 was at room temperature upon entering the top of the reactor.

This was followed by another regeneration, with the temperature of the Selexsorb adsorbent held above 400° F. Much less acetontrile was observed in these samples. The data are given in the Table.

TABLE

Results of Adsorption/Removal of Acetonitrile (ACN)

|  | Feed | 2 Hr. Effluent | 4 hr. Effluent | Regeneration #1 | | | | Regeneration #2 | | | |
| --- | --- | --- | --- | --- | --- | --- | --- | --- | --- | --- | --- |
|  |  |  |  | 15 min. | 30 min. | 45 min. | 60 min. | 15 min. | 30 min. | 45 min. | 60 min. |
| ACN (ppm) in Reactor Outlet | 605 | 42 | 140 | 588 | 79 | 33 | 24 | 36 | 3 | <1 | <1 |
| Sample Weight (g) | 28.7 | 25.35 | 28.43 | 25.26 | 25.56 | 25.80 | 25.45 | 25.21 | 25.24 | 25.18 | 26.39 |
| Temp. (° F.) | Ambient | 90.5 | 90.5 | 399.4 | 316.8 | 369.4 | 372.5 | 497.7 | 408.0 | 413.7 | 408.0 |
| Total ACN Charged to Reactor (g) | — | 0.091 | 0.091 | — | — | — | — | — | — | — | — |
| Total ACN in Reactor Outlet (g) | — | 0.006 | 0.042 | 0.046 | 0.006 | 0.003 | 0.002 | 0.003 | 0 | 0 | 0 |
| Cumulative ACN Adsorbed on Adsorbent (g) | — | 0.085 | 0.132 | — | — | — | — | — | — | — | — |
| iC$_5$ Added During ACN Removal (g) | — | — | — | 78.1 | 78.1 | 78.1 | 78.1 | 78.1 | 78.1 | 78.1 | 78.1 |
| Cumulative Total ACN Removed from Adsorbent (g) | — | — | — | 0.046 | 0.052 | 0.055 | 0.057 | 0.060 | 0.060 | 0.060 | 0.060 |
| Cumulative % ACN Removed from Adsorbent During Regeneration | — | — | — | 35 | 39 | 42 | 43 | 45 | 45 | 45 | 45 |

The amount of ACN recovered in the isopentane stripping stream was less than that adsorbed by the Selexsorb adsorbent. It is likely that some of the adsorbed ACN was converted to acetic acid and ammonia by reaction with the adsorbed water from the molecular sieve 3A during the regeneration step.

Following the second regeneration, the adsorbent was subjected to a combustion analysis wherein the combustion products were analyzed for carbon, hydrogen, nitrogen and sulfur and showed no detectable nitrogen (<0.15 wt. %). This indicates even better ACN removal (~100%) than was determined using the GC method.

The data indicate that Selexsorb adsorbent can remove acetonitrile from olefinic feedstocks and that regeneration of the Selexsorb adsorbent with iC5 at temperatures of up to about 500° F. can remove all of the adsorbed acetonitrile from spent Selexsorb.

Whereas this invention has been described in terms of the preferred embodiments, reasonable variations and modifications are possible by those skilled in the art. Such modifications are within the scope of the described invention and appended claims.

That which is claimed is:

1. A method of treating a hydrocarbon stream containing at least one heteroatom-containing compound and water, said method comprising the steps of:
   (a) introducing a hydrocarbon stream containing at least one heteroatom-containing compound and water to a contacting zone containing a water adsorbent comprising a molecular sieve having an average pore diameter in the range of from about 3 to about 4 Å, and a separate, heteroatom-containing compound adsorbent comprising an alumina and a zeolite;
   (b) withdrawing an effluent stream from said contacting zone, said effluent stream containing less heteroatom-containing compound and less water than said hydrocarbon stream;
   (c) blocking the introduction of said hydrocarbon stream to said contacting zone;
   (d) introducing a stripping stream comprising an isoparaffin to said contacting zone such that said stripping stream contacts said water adsorbent prior to contacting said heteroatom-containing compound adsorbent; and
   (e) withdrawing a spent stripping stream comprising isoparaffin, heteroatom-containing compound and water from said contacting zone.

2. A method in accordance with claim 1 wherein said stripping stream contacts said water adsorbent and said heteroatom-containing compound adsorbent at a temperature in the range of from about 350° F. to about 500° F.

3. A method in accordance with claim 1 wherein said stripping stream contacts said water adsorbent and said heteroatom-containing compound adsorbent for a time period in the range of from about 0.2 to about 2 hours.

4. A method in accordance with claim 1 further characterized to include the steps of:
   (f) cooling said spent stripping stream to form a cooled spent stripping stream;
   (g) introducing said cooled spent stripping stream to a settler for separation into a hydrocarbon phase and a water phase;
   (h) removing a portion of said hydrocarbon phase from said settler to form a circulating hydrocarbon stream;
   (i) mixing said circulating hydrocarbon stream with water to form a hydrocarbon/water mixture;
   (j) introducing said hydrocarbon/water mixture to said settler for separation into said hydrocarbon phase and said water phase;
   (k) removing a portion of said hydrocarbon phase from said settler to form a recycle isoparaffin stream, wherein said recycle isoparaffin stream contains less water and less heteroatom-containing compound as compared to said cooled spent stripping stream; and (l) using at least a portion of said recycle isoparaffin stream as at least a portion of said stripping stream.

5. A method in accordance with claim 4 further characterized to include:

removing at least a portion of said water phase from said settler to form a wastewater stream comprising water and heteroatom-containing compound.

6. A method in accordance with claim 4 wherein the cooling of step (f) is such that substantial portions of the water and of the heteroatom-containing compound contained in said spent stripping stream are condensed.

7. A method in accordance with claim 4 wherein said circulating hydrocarbon stream comprises isoparaffin and heteroatom-containing compound.

8. A method in accordance with claim 1 further characterized to include the steps of:

blocking the introduction of said stripping stream to said contacting zone in step (d);

reintroducing said hydrocarbon stream to said contacting zone; and withdrawing said effluent stream from said contacting zone.

9. A method in accordance with claim 1 wherein said hetero atom-containing compound contains sulfur.

10. A method in accordance with claim 1 wherein said hetero atom-containing compound contains nitrogen.

11. A method in accordance with claim 1 wherein said heteroatom-containing compound contains oxygen.

12. A method in accordance with claim 1 wherein said heteroatom-containing compound is a compound selected from the group consisting of acetonitrile, acetone, and combinations thereof.

13. A method in accordance with claim 1 wherein said heteroatom-containing compound is acetonitrile.

14. A method in accordance with claim 1 wherein said heteroatom-containing compound is acetone.

15. A method in accordance with claim 1 wherein said hydrocarbon stream is further characterized to comprise a compound selected from the group consisting of an olefin, an isoparaffin, and combinations thereof.

16. A method in accordance with claim 1 wherein said isoparaffin of said stripping stream contains in the range of from 3 to 5 carbon atoms per molecule, and mixtures thereof.

17. A method of regenerating a hydrocarbon purification system suitable for removing water and at least one heteroatom-containing compound from a hydrocarbon stream, said method for regenerating comprising:

(a) introducing a stripping stream comprising an isoparaffin into the contacting zone of a treatment system containing (1) a water adsorbent comprising a molecular sieve having an average pore diameter in the range of from about 3 to about 4 Å, which contains water, and (2) a separate, heteroatom-containing compound adsorbent comprising an alumina and a zeolite which contains a heteroatom-containing compound; such that said stripping stream contacts said water adsorbent prior to contacting said heteroatom-containing compound adsorbent; and (b) withdrawing a spent stripping stream comprising isoparaffin, heteroatom-containing compound and water from said contacting zone.

18. A method in accordance with claim 17 wherein said stripping stream contacts said water adsorbent and said heteroatom-containing compound adsorbent at a temperature in the range of from about 350° F. to about 500° F.

19. A method in accordance with claim 17 wherein said stripping stream contacts said water adsorbent and said heteroatom-containing compound adsorbent for a time period in the range of from about 0.2 to about 2 hours.

20. A method in accordance with claim 17 further characterized to include the steps of:

(c) cooling said spent stripping stream to form a cooled spent stripping stream;

(d) introducing said cooled spent stripping stream to a settler for separation into a hydrocarbon phase and a water phase;

(e) removing a portion of said hydrocarbon phase from said settler to form a circulating hydrocarbon stream;

(f) mixing said circulating hydrocarbon stream with water to form a hydrocarbon/water mixture;

(g) introducing said hydrocarbon/water mixture to said settler for separation into said hydrocarbon phase and said water phase;

(h) removing a portion of said hydrocarbon phase from said settler to form a recycle isoparaffin stream, wherein said recycle isoparaffin stream contains less water and less heteroatom-containing compound as compared to said cooled spent stripping stream; and (i) using at least a portion of said recycle isoparaffin stream as at least a portion of said stripping stream.

21. A method in accordance with claim 20 further characterized to include:

removing at least a portion of said water phase from said settler to form a wastewater stream comprising water and heteroatom-containing compound.

22. A method in accordance with claim 20 wherein the cooling of step (c) is such that substantial portions of the water and of the heteroatom-containing compound contained in said spent stripping stream are condensed.

23. A method in accordance with claim 20 wherein said circulating hydrocarbon stream comprises isoparaffin and heteroatom-containing compound.

24. A method in accordance with claim 17 wherein said heteroatom-containing compound contains sulfur.

25. A method in accordance with claim 17 wherein said heteroatom-containing compound contains nitrogen.

26. A method in accordance with claim 17 wherein said heteroatom-containing compound contains oxygen.

27. A method in accordance with claim 17 wherein said heteroatom-containing compound is a compound selected from the group consisting of acetonitrile, acetone, and combinations thereof.

28. A method in accordance with claim 17 wherein said heteroatom-containing compound is acetonitrile.

29. A method in accordance with claim 17 wherein said heteroatom-containing compound is acetone.

30. A method in accordance with claim 17 wherein said hydrocarbon stream is further characterized to comprise a compound selected from the group consisting of an olefin, an isoparaffin, and combinations thereof.

31. A method in accordance with claim 17 wherein said isoparaffin contains in the range of from 3 to 5 carbon atoms per molecule, and mixtures thereof.

32. A method of treating a hydrocarbon stream containing at least one heteroatom-containing compound and water, said method comprising the steps of:

(a) introducing a hydrocarbon stream containing at least one heteroatom-containing compound and water to a contacting zone containing a water adsorbent consisting essentially of a molecular sieve having an average pore diameter in the range of from about 3 to about 4 Å, and a separate, heteroatom-containing compound adsorbent consisting essentially of an alumina and a zeolite;

(b) withdrawing an effluent stream from said contacting zone, said effluent stream containing less heteroatom-containing compound and less water than said hydrocarbon stream;

(c) blocking the introduction of said hydrocarbon stream to said contacting zone;

(d) introducing a stripping stream comprising an isoparaffin to said contacting zone such that said stripping stream contacts said water adsorbent prior to contacting said heteroatom-containing compound adsorbent; and (e) withdrawing a spent stripping stream comprising isoparaffin, heteroatom-containing compound and water from said contacting zone.

33. A method in accordance with claim 32 wherein said stripping stream contacts said water adsorbent and said heteroatom-containing compound adsorbent at a temperature in the range of from about 350° F. to about 500° F.

34. A method in accordance with claim 32 wherein said stripping stream contacts said water adsorbent and said heteroatom-containing compound adsorbent for a time period in the range of from about 0.2 to about 2 hours.

35. A method in accordance with claim 32 further characterized to include the steps of:

(f) cooling said spent stripping stream to form a cooled spent stripping stream;

(g) introducing said cooled spent stripping stream to a settler for separation into a hydrocarbon phase and a water phase;

(h) removing a portion of said hydrocarbon phase from said settler to form a circulating hydrocarbon stream;

(i) mixing said circulating hydrocarbon stream with water to form a hydrocarbon/water mixture;

(j) introducing said hydrocarbon/water mixture to said settler for separation into said hydrocarbon phase and said water phase;

(k) removing a portion of said hydrocarbon phase from said settler to form a recycle isoparaffin stream, wherein said recycle isoparaffin stream contains less water and less heteroatom-containing compound as compared to said cooled spent stripping stream; and (l) using at least a portion of said recycle isoparaffin stream as at least a portion of said stripping stream.

36. A method in accordance with claim 35 further characterized to include:

removing at least a portion of said water phase from said settler to form a wastewater stream comprising water and heteroatom-containing compound.

37. A method in accordance with claim 35 wherein the cooling of step (f) is such that substantial portions of the water and of the heteroatom-containing compound contained in said spent stripping stream are condensed.

38. A method in accordance with claim 35 wherein said circulating hydrocarbon stream comprises isoparaffin and heteroatom-containing compound.

39. A method in accordance with claim 32 further characterized to include the steps of:

blocking the introduction of said stripping stream to said contacting zone in step (d);

reintroducing said hydrocarbon stream to said contacting zone; and withdrawing said effluent stream from said contacting zone.

40. A method in accordance with claim 32 wherein said heteroatom-containing compound contains sulfur.

41. A method in accordance with claim 32 wherein said heteroatom-containing compound contains nitrogen.

42. A method in accordance with claim 32 wherein said heteroatom-containing compound contains oxygen.

43. A method in accordance with claim 32 wherein said heteroatom-containing compound is a compound selected from the group consisting of acetonitrile, acetone, and combinations thereof.

44. A method in accordance with claim 32 wherein said heteroatom-containing compound is acetonitrile.

45. A method in accordance with claim 32 wherein said heteroatom-containing compound is acetone.

46. A method in accordance with claim 32 wherein said hydrocarbon stream is further characterized to comprise a compound selected from the group consisting of an olefin, an isoparaffin, and combinations thereof.

47. A method in accordance with claim 32 wherein said isoparaffin of said stripping stream contains in the range of from 3 to 5 carbon atoms per molecule, and mixtures thereof.

48. A method of regenerating a hydrocarbon purification system suitable for removing water and at least one heteroatom-containing compound from a hydrocarbon stream, said method for regenerating comprising:

(a) introducing a stripping stream comprising an isoparaffin into the contacting zone of a treatment system containing (1) a water adsorbent consisting essentially of a molecular sieve having an average pore diameter in the range of from about 3 to about 4 Å, which contains water, and (2) a separate, heteroatom-containing compound adsorbent consisting essentially of an alumina and a zeolite which contains a heteroatom-containing compound; such that said stripping stream contacts said water adsorbent prior to contacting said heteroatom-containing compound adsorbent; and (b) withdrawing a spent stripping stream comprising isoparaffin, heteroatom-containing compound and water from said contacting zone.

49. A method in accordance with claim 48 wherein said stripping stream contacts said water adsorbent and said heteroatom-containing compound adsorbent at a temperature in the range of from about 350° F. to about 500° F.

50. A method in accordance with claim 48 wherein said stripping stream contacts said water adsorbent and said heteroatom-containing compound adsorbent for a time period in the range of from about 0.2 to about 2 hours.

51. A method in accordance with claim 48 further characterized to include the steps of:

(c) cooling said spent stripping stream to form a cooled spent stripping stream;

(d) introducing said cooled spent stripping stream to a settler for separation into a hydrocarbon phase and a water phase;

(e) removing a portion of said hydrocarbon phase from said settler to form a circulating hydrocarbon stream;

(f) mixing said circulating hydrocarbon stream with water to form a hydrocarbon/water mixture;

(g) introducing said hydrocarbon/water mixture to said settler for separation into said hydrocarbon phase and said water phase;

(h) removing a portion of said hydrocarbon phase from said settler to form a recycle isoparaffin stream, wherein said recycle isoparaffin stream contains less water and less heteroatom-containing compound as compared to said cooled spent stripping stream; and (i) using at least a portion of said recycle isoparaffin stream as at least a portion of said stripping stream.

52. A method in accordance with claim 51 further characterized to include:

removing at least a portion of said water phase from said settler to form a wastewater stream comprising water and heteroatom-containing compound.

53. A method in accordance with claim 51 wherein the cooling of step (c) is such that substantial portions of the water and of the heteroatom-containing compound contained in said spent stripping stream are condensed.

54. A method in accordance with claim 51 wherein said circulating hydrocarbon stream comprises isoparaffin and heteroatom-containing compound.

55. A method in accordance with claim 48 wherein said heteroatom-containing compound contains sulfur.

56. A method in accordance with claim 48 wherein said heteroatom-containing compound contains nitrogen.

57. A method in accordance with claim 48 wherein said heteroatom-containing compound contains oxygen.

58. A method in accordance with claim 48 wherein said heteroatom-containing compound is a compound selected from the group consisting of acetonitrile, acetone, and combinations thereof.

59. A method in accordance with claim 48 wherein said heteroatom-containing compound is acetonitrile.

60. A method in accordance with claim 48 wherein said heteroatom-containing compound is acetone.

61. A method in accordance with claim 48 wherein said hydrocarbon stream is further characterized to comprise a compound selected from the group consisting of an olefin, an isoparaffin, and combinations thereof.

62. A method in accordance with claim 48 wherein said isoparaffin contains in the range of from 3 to 5 carbon atoms per molecule, and mixtures thereof.

\* \* \* \* \*